United States Patent [19]

Muller et al.

[11] 4,356,266

[45] Oct. 26, 1982

[54] PROCESS FOR THE HYDROLYSIS OF STARCH AND FERMENTABLE HYDROLYSATES OBTAINED THEREFROM

[75] Inventors: Werner C. Muller, Dobbs Ferry, N.Y.; Franklyn D. Miller, Cincinnati, Ohio

[73] Assignee: National Distillers & Chemical Corp., New York, N.Y.

[21] Appl. No.: 178,335

[22] Filed: Aug. 15, 1980

Related U.S. Application Data

[63] Continuation-in-part of Ser. No. 43,191, May 29, 1979, abandoned.

[51] Int. Cl.$^3$ .......................... C12P 7/14; C12P 19/14; C12P 19/20
[52] U.S. Cl. ...................................... 435/162; 435/96; 435/99; 435/819
[58] Field of Search ..................... 435/99, 96, 161–165, 435/819

[56] References Cited

U.S. PATENT DOCUMENTS 3,337,414 8/1967 Wilson .................................. 435/96
4,132,595 1/1979 Hebeda et al. ........................ 435/96

Primary Examiner—Lionel M. Shapiro
Attorney, Agent, or Firm—Kenneth D. Tremain

[57] ABSTRACT

An aqueous starch slurry is hydrolyzed in sequential liquefication and saccharification steps to provide saccharified starch containing from about 60 to about 80 weight percent of fermentable sugar based on the weight of the original starch present. Further saccharification is carried out either in one or more fermentation vessels wherein conversion of the sugar to ethanol simultaneously takes place or in one or more additional saccharification vessels.

26 Claims, 1 Drawing Figure

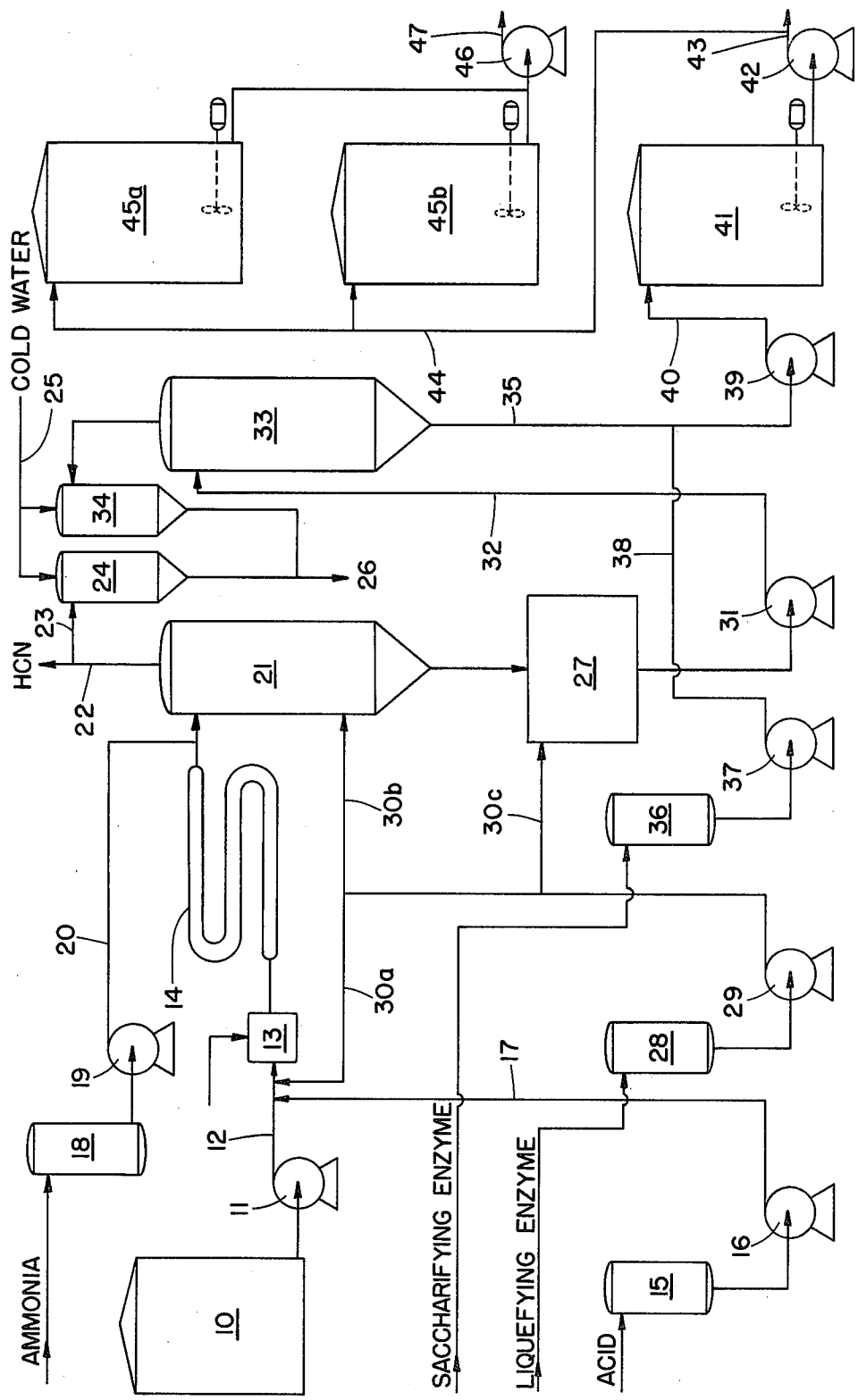

PROCESS FOR THE HYDROLYSIS OF STARCH AND FERMENTABLE HYDROLYSATES OBTAINED THEREFROM

CROSS REFERENCE TO RELATED APPLICATION

This application is a continuation in part of copending U.S. patent application Ser. No. 043,191, filed May 29, 1979, now abandoned and relates to commonly assigned copending U.S. patent application Ser. No. 043,193 filed May 29, 1979, now U.S. Pat. No. 4,243,750 issued Jan. 6, 1981.

BACKGROUND OF THE INVENTION

1. Field of the Invention

This invention relates to processes for the enzyme hydrolysis of starches and more particularly, to such processes especially adapted to provide substrate sugars for the fermentation of ethanol.

2. Description of the Prior Art

With the ever-increasing depletion of economically recoverable petroleum reserves, the production of ethanol from vegetative sources as a partial or complete replacement for conventional fossil-based liquid fuels becomes more attractive. In some areas, the economic and technical feasibility of using a 90% unleaded gasoline-10% anhydrous ethanol blend ("gasohol") has shown encouraging results. According to a recent study, gasohol powered automobiles have averaged a 5% reduction in fuel compared to unleaded gasoline powered vehicles and have emitted one-third less carbon monoxide than the latter. In addition to offering promise as a practical and efficient fuel, biomass-derived ethanol in large quantities and at a competitive price has the potential in some areas for replacing certain petroleum-based chemical feedstocks. Thus, for example, ethanol can be catalytically dehydrated to ethylene, one of the most important of all chemical raw materials both in terms of quantity and versitility.

The various operations in processes for obtaining ethanol from such recurring sources as cellulose, cane sugar, amylaceous grains and tubers, e.g., the separation of starch granules from non-carbohydrate plant matter and other extraneous substances, the chemical and/or enzymatic hydrolysis of starch to fermentable sugar (liquefaction and saccharification), the fermentation of sugar to a dilute solution of ethanol ("beer") and the recovery of anhydrous ethanol by distillation, have been modified in numerous ways to achieve improvements in product yield, production rates and so forth. For ethanol to realize its vast potential as a partial or total substitute for petroleum fuels or as a substitute chemical feedstock, it is necessary that the manufacturing process be as efficient in the use of energy as possible so as to maximize the energy return for the amount of ethanol produced and enhance the standing of the ethanol as an economically viable replacement for petroleum based raw materials. To date, however, relatively little concern has been given to the energy requirements for manufacturing ethanol from biomass and consequently, little effort has been made to minimize the thermal expenditure for carrying out any of the discrete operations involved in the manufacture of ethanol from vegetative sources.

The substitution of alcohol for at least a portion of petroleum based fuels is particularly critical for developing economies where proven domestic petroleum reserves are limited, such as in India and Brazil and these nations have therefore increasingly emphasized the production of alcohol from vegetative sources. The most common such operation employs cane sugar in a fermentation-distillation operation which conveniently utilizes the bagasse by-product as a fuel source. Cassava or manioc (*Manihot utilissima Pohl*) as a source of starch has also been considered for conversion into alcohol (see "Brazil's National Alcohol Programme", Jackson, ed. *Process Biochemistry*, June, 1976 pages 29–30; "Ethyl Alcohol from Cassava", Teixeira et al. *Industrial and Engineering Chemistry* pp. 1781–1783 (1950); and United Kingdom Patent Specification No. 1,277,002). However, since manioc lacks the equivalent of sugar cane's bagasse, the fuel for alcohol conversion must come from an external source. Thus, to make manioc root an economically attractive source of ethanol, it is essential to achieve rapid and high levels of conversion of the starch content to fermentable saccharide and of the fermentable saccharide to ethanol with high levels of thermal efficiency and at conservative plant investment and operating costs.

Processes for the liquefaction and saccharification of starch to provide fermentable saccharides are well known (viz., U.S. Pat. Nos. 2,219,668; 2,289,808; 2,356,218; 2,431,004; 2,676,905; 2,954,304; 3,308,037; 3,337,414; 3,423,239; 3,425,909; 3,551,293; 3,565,764; 3,591,454; 3,592,734; 3,654,081; 3,720,583; 3,910,820; 3,912,590; 3,922,196; 3,922,197; 3,922,198; 3,922,199; 3,922,200; 3,922,201; 3,969,538; 3,988,204; 3,922,261; 3,966,107; 3,998,696; 4,014,743; 4,016,038; 4,017,363; 4,028,186; 4,032,403; and 4,132,595; see also, Novo Industri A/S (DK-2880 Bagsvaerd, Denmark) brochures entitled "Dextrose and Starch Sugar", "Conversion of Starch" and "Glucose Syrups"). The hydrolysis of manioc root starch with mineral acid preparative to fermentation of the resulting sugar to produce ethanol has been investigated (see "Tapioca as a Source of Alcohol", Krishnamurti, E. G. 1960, *Current Science* 9:346-348). However, the hydrolysis resulted in the consumption of acid and additional hydrolysis could not be effected without the addition of fresh acid. Moreover, under the conditions employed (heating at 50–60 p.s.i. with 2% sulfuric acid for 4 hours), the hydrolyzed starch solution developed a dark color and a burnt smell which would signal saccharide degradation. Hydrolysis of the starch with lower amounts of sulfuric acid, i.e., 0.5% and 1.0% respectively, under the foregoing conditions failed to provide complete hydrolysis.

The composition of manioc is similar to other tropical starchy roots in that the bulk of the dried matter is carbohydrate, about 66–72% of which is starch in the form of granules of about 5 to $35\mu$ in dimension. Starch granules comprise amylose, a straight chain polymerized maltose, and amylopectin, a branched chain polymerized maltose. However, cassava starch is distinguished from common sources of starch by its relatively low content, e.g., 17%, of amylose as compared to potato starch (22%) and corn starch (27%). Its corresponding relatively large percentage of branched chain amylopectin imparts different properties; and yet it is not a typical amylopectin starch, rendering its treatment as in saccharification somewhat unique.

Accordingly, there has heretofore existed a need for a process for hydrolyzing manioc root starch and starches obtained from other sources at rapid and high levels of conversion without any significant degradation of the resulting saccharide and at only a modest expenditure of thermal energy.

SUMMARY OF THE INVENTION

In accordance with the present invention, an aqueous slurry of starch is hydrolyzed to fermentable ethanol in three distinct steps or phases, namely a liquefaction step followed by two saccharification steps. In the liquefaction step, the starch is converted to a pumpable partial hydrolysate, substantially in the absence of added starch hydrolysate, employing a liquefying agent selected from the group consisting of strong acid and liquefying enzyme. The liquefied starch which contains higher sugars but relatively small amounts of fermentable sugar is partially saccharified in a primary or preliminary saccharification vessel or vessels in the presence of a saccharifying enzyme for a period of time sufficient to convert from about 60 to about 80 weight percent of the original starch present (calculated on a dry basis) to fermentable sugar with the remaining portion of the original starch being present in the form of partial hydrolysate. The mixture of fermentable sugar and partial hydrolysate resulting from the primary saccharification is then introduced into a secondary or finishing saccharification vessel or vessels wherein further saccharification of the partial hydrolysate alone is carried out. In a preferred embodiment of the present invention, the secondary saccharification is carried out in a fermentation vessel to wherein the fermentable sugar is converted to ethanol simultaneously with the completion of saccharification. Liquefaction is rapidly accomplished at elevated temperature and pressure employing a strong acid such as hydrochloric acid to effect partial hydrolysis, a liquefying enzyme such as alpha-amylase or a two-step procedure employing acid for initial liquefaction and liquefying enzyme for further liquefaction. Following the cooling and reduction in pressure of the liquefied starch, saccharification is carried out in the presence of a dextrogenic enzyme such as amyloglucosidase to achieve still a higher conversion of starch to fermentable sugar. To minimize the amount of equipment required to process a given amount of starch, the volume of the secondary saccharification vessel(s) will ordinarily only be as large as is necessary to accommodate the amount of starch which was previously partially hydrolyzed in the first saccharification vessel(s).

When acid is used in the liquefaction step, neutralization of the partially hydrolyzed starch medium prior to the addition of any enzymes which effect further liquefaction and/or saccharification is generally necessary as the enzymes work best only at higher levels of pH. It is a feature of the present invention to employ at least one acid selected from the group consisting of nitric acid, sulfuric acid, hydrochloric acid and phosphoric acid in the liquefaction stage and neutralizing the acid with ammonia prior to the addition of enzyme to accomplish further hydrolysis of the starch. The ammonium salt which is formed as a result of the neutralization of the liquefying acid is retained in the fermentable sugar liquid and serves to satisfy part of the nutritive requirements of the yeast employed in the fermentation of the sugar liquid to ethanol.

While the process of the invention herein is especially advantageous for converting manioc root starch to fermentable sugar, the process is equally applicable to the hydrolysis of starch from other sources such as corn, sorghum, wheat, potatoes, rice, milo and the like.

The term "strong acid" as employed herein refers to any of the inorganic acids having a pKa value of at least about 2.5 or less. The term "fermentable sugar" should be understood as referring to a single fermentable sugar such as glucose (dextrose), fructose, maltose or sucrose but more commonly will be applicable to these and similar fermentable saccharides in admixture.

While in some respects the process herein may be considered to bear a resemblance to the multi-stage enzymatic starch hydrolysis process described in U.S. Pat. No. 3,337,414, there are several fundamental differences between the two procedures. In the present invention, the starch is subjected to liquefaction employing acid and/or enzyme prior to actual saccharification. This liquefaction results in a readily pumpable liquid in which depolymerization of the starch has already progressed to a significant extent. In contrast to this, the process of U.S. Pat. No. 3,337,414 merely pastes the starch and does not achieve any partial hydrolysis of the pasted starch until the latter is thinned with partial hydrolyzate recycled from the primary enzymatic convertor. Not only does recycling of partially hydrolyzed starch necessarily reduce the overall rate of conversion of the starch to fermentable sugar and complicate the apparatus required for such conversion, it poses the additional disadvantage that, prior to thinning with recycled hydrolyzate, the pasted starch can reach a viscosity which is beyond the working capacity of the pumping system. Excessive burning of the pasted starch and/or undesirable equipment down-time can result in such a situation. Since the aqueous starch slurry feed of the present invention is never in a merely pasted condition but is liquefied for convenient pumping, the aforementioned drawbacks of the process of U.S. Pat. No. 3,337,414 are entirely avoided.

BRIEF DESCRIPTION OF THE DRAWING

The accompanying drawing is a diagrammatic flow sheet illustrative of one embodiment of a starch hydrolysis process in accordance with the present invention.

DESCRIPTION OF THE PREFERRED EMBODIMENTS

Referring to the drawing, a concentrated aqueous slurry of manioc root starch (or starch from any other source) which contains from about 20 to about 50 weight percent dry substance (D.S.), and preferably from about 30 to about 40 weight percent D.S., and which may also contain other components of the root such as water soluble proteins, fats, sugars and minerals and/or water insoluble materials such as fiber, minute amounts of soil, gravel, etc., is delivered from starch slurry tank 10 by pump 11 through line 12 to steam jet mixer 13 where it is combined with steam and thereafter passed through starch liquefier 14 where partial hydrolysis of the starch substantially in the absence of added starch hydrolysate takes place. Pump 11 provides a discharge pressure which is substantially greater than the saturation pressure of steam at the temperature to which the slurry is heated in starch liquefier 14. Prior to introduction into steam jet mixer 13, the starch slurry is combined with a strong acid as partial, but preferably, exclusive liquefying agent to provide a pH of from about 1.0 to about 2.5, and preferably from about 1.2 to 2.2. Suitable acids include nitric acid, sulfuric acid, hydrochloric acid and phosphoric acid. The acid is supplied from storage vessel 15 where it is moved by pump 16 through line 17 to be mixed with the starch slurry passing through line 12. When employing acid as the liquefying agent, the amount of steam introduced into the starch slurry through steam jet mixer 13 is sufficient to provide a temperature in starch liquefier 14 which is in the range of from about 160° F. to about 350° F., in which range the pressure of the steam can vary from about 25 psig to about 250 psig. Preferably, starch liquefier 14 is operated within the range of from about 200° F. to about 250° F. and at a pressure of from about 50 to about 150 psig. Residence time of the acidified starch slurry in liquefier 14 to effect partial hydrolysis and sterilization of the starch can vary from about 2 to about 15 minutes and preferably from 5 to about 10 minutes. Emerging from liquefier 14, the acidified starch is neutralized with liquid or aqueous ammonia conveyed from tank 18 by pump 19 through line 20. When initial starch liquefaction is accomplished with acid followed by a further liquefaction with enzyme, the pH of the neutralized slurry will advantageously be adjusted to a level which promotes optimum enzymatic activity in the liquefying enzyme which is later added to the initially liquefied starch in flash tank 21 or holding tank 27 to complete liquefaction. For many liquefying enzymes, the pH of the neutralized liquefied starch is advantageously within the range of from about 3.0 to about 6.0 and preferably from about 4.0 to about 5.0. The ammonium nitrate, sulfate, chloride and/or phosphate which is produced by neutralization of the acid liquefying agent(s) is retained in the product fermentable sugar liquid produced by the process herein in order to satisfy a nutritional need of the yeast which is used for the conversion of the sugars to ethanol. Subsequent to neutralization, the initially liquefied starch is introduced into flash tank 21 where steam is flashed to adiabatically cool the liquid mass, preferably to about 212° F. The vapors discharged from flash tank 21 through line 22 contain a small amount of hydrogen cyanide gas generated from the hydrolysis of cyanogenic glucosides present in the manioc root. These vapors may, if local regulations permit, be discharged therefrom to the upper atmosphere with the aid of steam. Alternatively, the vapors are passed through line 23 into direct contact water jet condenser 24 supplied with cold water through line 25, with the liquid condensate passing to sump sewer 26. In the event the cooled depressurized liquefied starch from flash tank 21 requires an enzymatic treatment to complete liquefaction, it is conveyed to holding tank 27 which may be integrated with atmospheric flash tank 21 to form a single unit or, as shown, may be provided as a separate vessel where enzymatic liquefaction is permitted to take place. The liquefied starch is combined with from about 0.3 to about 2.0 lb. per 1000 lb. of dry starch, and preferably from about 0.5 to about 1.0 lb. per 1000 lb. of dry starch, of liquefying enzyme such as alpha-amylase delivered from storage vessel 28 by pump 29 through line 30 ($b$) to flash tank 21 or through line 30 ($c$) to holding tank 27. The enzyme-containing partial hydrolysate is held at about 212° F. in holding tank 27 for from about five minutes to about three hours or until a level of from about 12 to about 24 dextrose equivalent (D.E.), and preferably from about 16 to about 20 D.E., has been attained. It is, of course, within the scope of this invention to employ acid as the sole starch liquefying agent in which case there will be no need to add enzyme to the cooled depressurized starch obtained in flash tank 21 nor will there be any need to provide a holding vessel such as holding tank 27.

It is further within the scope of this invention to employ liquefying enzyme exclusively for the liquefaction step thereby dispensing with an acid neutralization procedure. In such a case, the entire amount of liquefying enzyme, e.g., from about 0.3 to about 3.0 lb. per 1000 lb. of dry starch and preferably from about 0.5 to about 1.0 lb. per 1000 lb. of dry starch, can be added to the starch slurry through line 30 ($a$) prior to the passage of the slurry through starch liquefier 14. Starch liquefier 14 is advantageously maintained at a temperature of from about 160° F. to about 250° F., and preferably at from about 200° F. to about 230° F. It is preferred to adjust the pH of the starch slurry, either before, with or following the addition of the liquefying enzyme, but before significant liquefaction has occurred, to a pH level of from about 3.0 to about 6.0, and preferably from about 4.0 to about 5.0, advantageously employing any of the aforementioned strong acids. However, since some of the liquefying enzyme may be inactivated or destroyed at the high operating temperature of starch liquefier 14, it is preferred to add only as much enzyme at this location as is needed to obtain a pumpable partially liquefied starch at the discharge end of the liquefier, e.g., from about $\frac{1}{4}$ to about $\frac{1}{3}$ the total amount, with the remaining amount of liquefying enzyme being added to the partially liquefied starch in flash tank 21 through line 30 ($b$) or in holding tank 27 through line 30 ($c$).

The liquefied starch from flash tank 21 (if an acid liquefaction alone was employed) or holding tank 27 (if enzymatic liquefaction or combined acid-enzymatic liquefaction was employed) is conveyed by pump 31 through line 32 to vacuum flash tank 33 where the liqud mass is further cooled to from about 130° F. to about 160° F., and preferably from about 140° F. to about 145° F. The vapors discharged from flash tank 33 are condensed in direct contact water jet condenser 34 supplied with cold water through line 25 to maintain a vacuum of from about 1 to about 5 psig, and preferably from about 2 to about 4, in flash tank 33. The liquid condensate from water jet condenser 34 passes to sump sewer 26. From vacuum flash tank 33, the liquefied starch passes through line 35 where it is combined with a saccharifying enzyme such as amyloglucosidase, preferably containing a saccharification catalyst such as a source of calcium ion, delivered from storage vessel 36 by pump 37 through line 38 and the saccharifying enzyme-containing liquefied starch is then delivered by pump 39 through line 40 into temperature regulated, agitated primary saccharification vessel 41. Prior to addition of the saccharifying enzyme, it is preferred to adjust the pH of the liquefied starch (to promote maximum enzyme activity) to a level of from about 4.0 to about 5.0, and more preferably to a level of from about 4.3 to 4.7. This will generally require the addition of base since the liquefied starch will usually be somewhat more acidic than the aforesaid pH ranges. It is preferred to employ ammonia or aqueous ammonia to accomplish the pH adjustment since the resulting ammonium salt will be a useful nutrient for the yeast which is used to convert the sugar liquid herein to ethanol. Saccharification in vessel 41 is advantageously maintained at a temperature which is most favorable to maximum enzyme activity, generally in the range of from about 140° F. to 145° F. The saccharification is permitted to proceed in vessel 41 only until such time as about 60 to about 70 weight percent fermentable sugar is obtained. Depending upon the saccharification conditions this level of fermented sugar can be reached within about two to about ten hours, and more usually, four to eight hours, of saccharifying time. In contrast to this, known and conventional saccharification processes are carried out in the same vessel until the maximum amount of fermentable sugar is obtained, i.e., about 92 to 96 weight percent. Since the rate of saccharification falls off rather abruptly after only about eight hours, such a high conversion level of liquefied starch to fermentable sugar can only be achieved over a fairly long period of time, generally from about 24 to 74 hours. These lengthy saccharifying times have not been of concern to the sugar and alcoholic beverage industries where starch conversion is widely practiced since the quality of the end product is of paramount concern. However, such saccharifying times are a serious obstacle to realizing an efficient and rapid process for providing low cost fermentable sugar which in turn will provide low cost ethanol upon fermentation. Since the saccharified liquid herein containing from about 60 to about 70 weight percent fermentable sugar can be conveyed from saccharification vessel 41 by pump 42 through line 43 directly into one or a series of fermentation vessels where ethanol production side-by-side with saccharification of the remaining partial hydrolysates of the starch takes place, from three to nine times as much starch can be effectively processed in accordance with the invention herein as in the processes of the prior art without requiring a multifold increase in plant equipment expenditure and operating costs. If desired, all or a part of the sugar liquid from primary saccharification 41 vessel can be conveyed by pump 42 through line 44 into one or more temperature regulated, agitated secondary saccharification vessels 45a and 45b where further saccharification can be carried out. The total volume $V_2$ of second saccharification vessels 45a and 45b must be at least equal to:

$$V_1(x/y)$$

wherein $V_1$ is the total volume of fermentation medium in primary saccharification vessel 41, x is the time period (e.g. number of hours) of saccharification in vessel 45a (which will be the same for vessel 45b) and y is the time period of saccharification in vessel 41. Thus, for example, when saccharification is carried out in vessel 41 for a period of eight hours and the hydrolysate therefrom is further saccharified in vessel 45a for a period of sixteen hours (i.e., for a fermentable sugar content of from about 85 to about 90 weight percent), the total volume of vessels 45a and 45b must be at least twice that of vessel 41 in order to accommodate the volume of liquid processed by primary saccharification vessel 41 over a period of sixteen hours. The combined sugar liquid from secondary saccharification vessels 45a and 45b is conveyed by pump 46 through line 47 either to one or more fermentation vessels for ethanol production or to storage. If storage is contemplated, the sugar liquid should be maintained at least about 140° F. to inhibit any repolymerization of partial hydrolysates contained therein (i.e., "starch retrogradation"). If a starch slurry is employed in the foregoing process which contains insoluble matter, such matter should be separated from the product sugar prior to the use of the latter in fermentation in order to prevent the accumulation of such matter in the fermentation vessel(s). The separation can be readily accomplished employing any of the known and conventional techniques such as filtration, centrifugation, etc.

Fermentation of the sugar liquid herein to provide ethanol is advantageously carried out by the fermentation process disclosed in commonly assigned copending U.S. patent application Ser. No. 043,190 filed May 29, 1979, now U.S. Pat. No. 4,242,454.

The following examples are further illustrative of the hydrolysis process of this invention.

EXAMPLE 1

A. Starch Liquefaction 1.0 ml of Termanyl 60L (an alpha-amylase liquefying enzyme from Novo Industri A/S) was added to 120° F. tap water. A 30 weight percent aqueous slurry of manioc root starch was added to the enzyme all at once, pH was adjusted to 6.5 and the mixture was heated from 200° F. to 220° F. for two hours in the absence of added starch hydrolyzate. Samples of the liquefied starch were taken at various time intervals, the amounts of reducing sugar and dextrose being measured as follows:

| Sample | Minutes | Temp. (°F.) | D.E.* Reducing sugar | D.E. Glucose |
|---|---|---|---|---|
|  | 0 | 115 |  |  |
| 1 | 20 | 185 | 20.44 | 13.85 |
| 2 | 30 | 205 | 20.53 | 17.08 |
| 3 | 70 | 212 | 20.24 | 18.97 |
| 4 | 110 | 212 | 22.56 | 18.23 |
| 5 | 150 | 212 | 27.54 | 18.63 |

*D.E. = Dextrose Equivalent

B. Saccharification of Liquefied Starch

The above liquefied starch samples were saccharified at 140° F. and a pH of 4.5 with 3 ml AMG 150L (an amyloglusidase saccharifying enzyme from Novo) per 1000 g. starch D.S. Samples of the saccharified starch were taken at various intervals, the amounts of reducing sugar and dextrose being measured as follows:

| Sample | Hours | Temp. (°F.) | D.E. Reducing sugar | D.E. Glucose |
|---|---|---|---|---|
| 1 | 0 | 140 | 28.59 | 20.60 |
| 2 | 2 | 140 | 69.31 | 58.15 |
| 3 | 4 | 140 | 82.46 | 74.48 |
| 4 | 6 | 144 | 88.92 | 76.24 |
| 5 | 21 | 144 | 94.93 | 82.58 |

EXAMPLE 2

A. Starch Liquefaction

The starch liquefaction procedure of Example 1 was repeated except that the starch was added, in equal amounts, in three steps, at times 0, 25 and 45 minutes. (The next portion of starch was added in dry form, when the viscosity of the dextrin in the reaction vessel had decreased). Assay was as follows:

| Sample | Minutes | Temp (°F.) | D.E. Reducing sugar | D.E. Glucose |
|---|---|---|---|---|
| 1 | 10 | 160 | 20.95 | 19.89 |
| 2 | 25 | 205 | 23.96 | 18.73 |
| 3 | 45 | 212 | 20.29 | 17.28 |
| 4 | 75 | 205 | 20.85 | 16.87 |
| 5 | 115 | 212 | 21.75 | 15.23 |

B. Saccharification of Liquefied Starch

Following the saccharification procedure of Example 1, the above liquefied starch samples were saccharified with the following results:

| Sample | Hours | Temp (°F.) | D.E. Reducing sugar | D.E. Glucose |
|---|---|---|---|---|
| 1 | 0 | 60.0 | 35.29 | 20.15 |
| 2 | 2 | 60.5 | 83.73 | 71.51 |
| 3 | 4 | 59.0 | 97.62 | 87.76 |
| 4 | 6 | 62.0 | 90.34 | 85.82 |
| 5 | 21 | 62.0 | 92.77 | 90.43 |

What is claimed is:

1. A process for the hydrolysis of starch to provide an aqueous solution of fermentable sugar which comprises:
   (a) liquefying an aqueous slurry of starch in the presence of a liquefying agent selected from the group consisting of strong acid and liquefying enzyme to provide sterile liquefied partially hydrolyzed starch;
   (b) partially saccharifying the liquefied partially hydrolyzed starch in a primary saccharification vessel or vessels in the absence of added starch hydrolysate in the presence of a saccharifying enzyme to provide sterile saccharified starch containing from about 60 to about 80 weight percent of the original starch in the form of fermentable sugar, the remaining portion of the starch being present in the form of partial hydrolysate; and,
   (c) further saccharifying the partially saccharified starch resulting from step (b) in a secondary vessel or vessels having a total volume of at least $V_2 = V_1 (x/y)$ wherein $V_1$ is the total volume of the fermentation medium in the primary saccharification vessel or vessels, $x$ is the period of saccharification in the secondary saccharification vessel or vessels and $y$ is the period of saccharification in the primary saccharification vessel or vessels.

2. The process of claim 1 wherein the starch is derived from manioc root.

3. The process of claim 2 wherein the hydrogen cyanide generated from the hydrolysis of cyanogenic glucosides during the liquefaction of the starch is substantially eliminated therefrom.

4. The process of claim 1 wherein the starch contains water soluble protein, fat, sugar, vitamines, and/or minerals.

5. The process of claim 1 wherein the starch contains water insoluble components which are removed prior to the consumption of the saccharified starch.

6. The process of claim 1 wherein strong acid is used exclusively to achieve liquefaction.

7. The process of claim 6 wherein the strong acid is at least one member of the group consisting of nitric acid, sulfuric acid, hydrochloric acid and phosphoric acid.

8. The process of claim 7 wherein ammonia or aqueous ammonia is added to the liquefaction starch to at least partially neutralize the acid and form at least one salt selected from the group consisting of ammonium nitrate, ammonium sulfate, ammonium chloride and ammonium phosphate.

9. The process of claim 8, wherein the pH of the neutralized liquefied starch is adjusted to from about 4.0 to about 5.0 prior to the addition of saccharifying enzyme.

10. The process of claim 9, wherein the pH of the neutralized liquefied starch is adjusted to from about 4.3 to about 4.7 prior to the addition of saccharifying enzyme.

11. The process of claim 1 wherein liquefying enzyme is used exclusively to achieve liquefaction.

12. The process of claim 11 wherein the pH of the aqueous starch slurry is adjusted to from about 3.0 to about 6.0 prior to, with, or following the addition of liquefying enzyme but before significant liquefaction has occurred.

13. The process of claim 11 wherein the pH of the aqueous starch slurry is adjusted to from about 4.0 to about 5.0 prior to, with, or following the addition of liquefying enzyme but before significant liquefaction has occurred.

14. The process of claim 12 wherein the pH is adjusted by use of a strong acid.

15. The process of claim 14 wherein the strong acid is selected from the group consisting of nitric acid, sulfuric acid, hydrochloric acid and phosphoric acid.

16. The process of claim 11 wherein the liquefying enzyme is alpha-amylase.

17. The process of claim 11 wherein only as much liquefying enzyme is added to the aqueous starch slurry prior to initial liquefaction as is necessary to provide a pumpable starch fluid following initial liquefaction, the remaining portion of the liquefying enzyme then being added to further liquefaction.

18. The process of claim 17 wherein from about ¼ to about ⅓ of the total amount of liquefying enzyme is added to the aqueous starch slurry to initiate liquefaction and from about ¾ to ⅔ of the total amount of liquefying enzyme is added to the initially liquefied starch to further liquefaction.

19. The process of claim 11, wherein the pH of the liquefied starch is adjusted, if necessary, to form about 4.0 to about 5.0 prior to the addition of saccharifying enzyme.

20. The process of claim 19, wherein the pH of the liquefied starch is adjusted, if necessary, to from about 4.3 to about 4.7 prior to the addition of saccharifying enzyme.

21. The process of claim 1 wherein strong acid is first used to accomplish initial liquefaction and liquefying enzyme is subsequently used to further liquefaction.

22. The process of claim 21 wherein the strong acid is at least one member of the group consisting of nitric acid, sulfuric acid, hydrochloric acid and phosphoric acid and the liquefying enzyme is alpha-amylase.

23. The process of claim 22 wherein ammonia or aqueous ammonia is added to the initially liquefied starch prior to addition of liquefying enzyme to at least partially neutralize the acid and form at least one salt selected from the group consisting of ammonium nitrate, ammonium sulfate, ammonium chloride and ammonium phosphate.

24. The process of claim 1 wherein the saccharifying enzyme is amyloglucosidase.

25. The process of claim 1 wherein the secondary vessel or vessels is one or a series of fermentors wherein conversion of fermentable sugar to ethanol simultaneously with further saccharification of partial hydrolyzate to fermentable sugar takes place.

26. The process of claim 1 wherein fermentation of the fermentable sugar produced in the secondary saccharification vessel or vessels to ethanol takes place in said vessel or vessels.

* * * * *